United States Patent [19]

Wick et al.

[11] 4,444,317

[45] Apr. 24, 1984

[54] OBSERVATION OF IMMUNOFLUORESCENE FOR DISTINGUISHING BETWEEN SPECIFIC AND NONSPECIFIC BINDING OF CONJUGATES

[76] Inventors: Georg Wick; Günther Böck; K. Schauenstein, all c/o Institute for General and Experimental Pathology, University of Innsbruck, Fritz-Pregl-Strasse 3, A-6020 Innsbruck, Austria

[21] Appl. No.: 296,562

[22] Filed: Aug. 26, 1981

[51] Int. Cl.$^3$ .................................................. B07C 5/02
[52] U.S. Cl. .................................... 209/3.1; 209/579; 209/906; 364/414; 356/338; 356/318
[58] Field of Search ................. 209/3.1, 3.2, 3.3, 44.1, 209/127 R, 127 C, 3, 128–130, 576, 577, 579, 906; 324/71.4; 356/72, 39, 318, 335, 336, 338; 250/222.2; 235/92 PC; 361/226; 364/414

[56] References Cited

U.S. PATENT DOCUMENTS

| 3,710,933 | 1/1973 | Fulwyler et al. | 209/3.1 |
| 4,081,530 | 3/1978 | Immer et al. | 424/177 |
| 4,110,043 | 8/1978 | Eisert | 356/336 |
| 4,136,950 | 1/1979 | Labrum et al. | 250/222.2 |
| 4,173,415 | 11/1979 | Wyatt | 356/336 |
| 4,195,930 | 4/1980 | Delhaye et al. | 356/318 |
| 4,279,345 | 7/1981 | Allred | 209/3.2 |
| 4,407,964 | 10/1983 | Elings et al. | 356/318 |

Primary Examiner—Allen N. Knowles
Assistant Examiner—Donald Hajec
Attorney, Agent, or Firm—Karl F. Ross; Herbert Dubno

[57] ABSTRACT

Disclosed are a method and a device for distinguishing particles or regions therein to which fluorochrome-labeled antibodies or antigens, termed conjugates, are bound by the specific immune reaction of an antibody with its homologous antigen from particles or regions to which the conjugates are nonspecifically bound. The method is based on the different bleaching behavior caused by the different types of binding. Use is made of a microscope whose entire field of view is conventionally illuminated, a central laser beam serving for bleaching analysis.

2 Claims, 5 Drawing Figures

Fig.1a
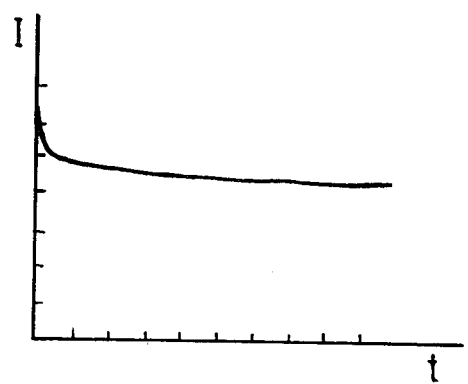
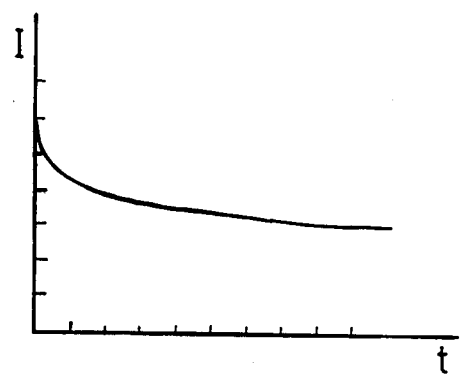
Fig.1b

OBSERVATION OF IMMUNOFLUORESCENE FOR DISTINGUISHING BETWEEN SPECIFIC AND NONSPECIFIC BINDING OF CONJUGATES

BACKGROUND OF THE INVENTION

Our present invention relates to a method and a device for distinguishing certain particles or regions therein, to which fluorochrome-labeled antibodies or antigens—termed conjugates are bound by the specific immune reaction of an antibody with its homologous antigen, from particles or regions to which the conjugates are nonspecifically bound.

BACKGROUND OF THE INVENTION

Immunofluorescence is a technique which allows the visualization of antigen-antibody reactions under a microscope using either fluorochrome-labeled antibody or antigen perparations. The most frequently used fluorochromes are derivatives of fluorescein (green fluorescence) and rhodamine (red fluorescence). For fluorescence excitation, mercury-vapor bulbs or Xenon lamps are usually attached to the microscope. From these sources light of the desired wavelength is selected by means of special filters, i.e. blue light for excitation of fluorescein derivatives and green light for excitation of rhodamine derivatives. One limitation of immunofluorescence is caused by the fact that it is so far impossible to distinguish specific fluorescence from so-called nonspecific fluorescence, the latter being due to nonspecific binding of conjugates to tissues, single cells, or other substrates such as insolubilized antigens on the surface of particles or other support materials.

In order to distinguish between the fluorescence caused by bound conjugates and the fluorescence of free fluorochrome it has already been proposed (Tomas Hirschfeld, "Fluorescence Background Discrimination by Prebleaching", The Journal of Histochemistry and Cytochemistry, Vol. 27, No. 1, pp. 96–101 1979) to observe the bleaching behavior of different samples during the first few milliseconds of exposure to a focused argon laser. In U.S. Pat. No. 4,081,530 the same purpose is achieved by integrating the fluorescent emission over the bleaching interval.

SUMMARY OF THE INVENTION

In comparison with this art the method of our invention is based on the observation that the bleaching behavior of conjugates during illumination with very short laser pulses can be used for the distinction not only of free and bound conjugates but also of specifically and nonspecifically bound states.

A feature of our invention consists, therefor, in illuminating the particles or regions with a laser, measuring the resulting fluorescence at three or more instants within the first three milliseconds after the beginning of such illumination while illumination continues, comparing the observed bleaching behavior of the particle or region with the characteristic curves for specific and nonspecific binding previously obtained by observation of other particles, and producing a signal indicating the type of binding observed.

To obtain the characteristic curves which serve as a standard for comparison, samples are used which are known to the free of antigen-antibody pairs and thus free of specific fluorescence. Other samples which are known to include antigen-antibody pairs will then yield an additional bleaching curve produced by the specifically bound conjugates. This latter curve shows a much smoother transition from a high initial fluorescence to a fairly constant intensity, reached after about three milliseconds, than is the case for nonspecifically bound particles.

The distinction between the two types of curves can easily be made by the observer. Of course, if it is desired to sort a great many particles according to the type of binding it will be necessary to use computers for attributing the bleaching curve of a certain particle to one of the two types of curves. For this purpose a simple algorithm has been developed according to which the fluorescence intensity (FI) is given by a curve according to the formula $$FI = \frac{a}{b+t} + c,$$

t being the time and a,b,c being constants characteristic for the individual curve. The constants a and b have been found to differ to about a factor of 10 for a specific and a nonspecific binding.

A further feature of our invention resides in a special microscope which may be used to carry out the process referred to. This microscope uses an argon laser attached to an immunofluorescence microscope as an additional source of illumination. The argon laser emits monochromatic high-energy light at 488 nm (blue) and 515 nm (green) that can thus be used for illumination of green and red fluorescence. The periods of illumination of the fluorescent preparation by the laser are timed by a shutter in the path of its beam.

The entire field of view is illuminated by a conventional light source, such as a mercury-vapor bulb. In the middle of this field the narrow laser beam is focused into the light path via a dichroic mirror.

In the area of the beam the fluorescence is about $10^2$ to $10^3$ times stronger than in the surrounding conventionally illuminated area.

This set-up allows to recognize the fluorescing particles or regions of tissue in the entire field of view without subjecting them to excessive irradiation before they are analyzed under the laser beam.

For the sorting of large numbers of particles we prefer to have a stream of particles moving through a stationary laser beam. The bleaching curve of each particle is then analyzed before the next particle arrives and a sorting mechanism is actuated depending on the result of the analysis.

BRIEF DESCRIPTION OF THE DRAWING

FIGS. 1a and 1b show the bleaching curves for specifically and nonspecifically bound conjugates, respectively;

SPECIFIC DESCRIPTION

Figure 2:
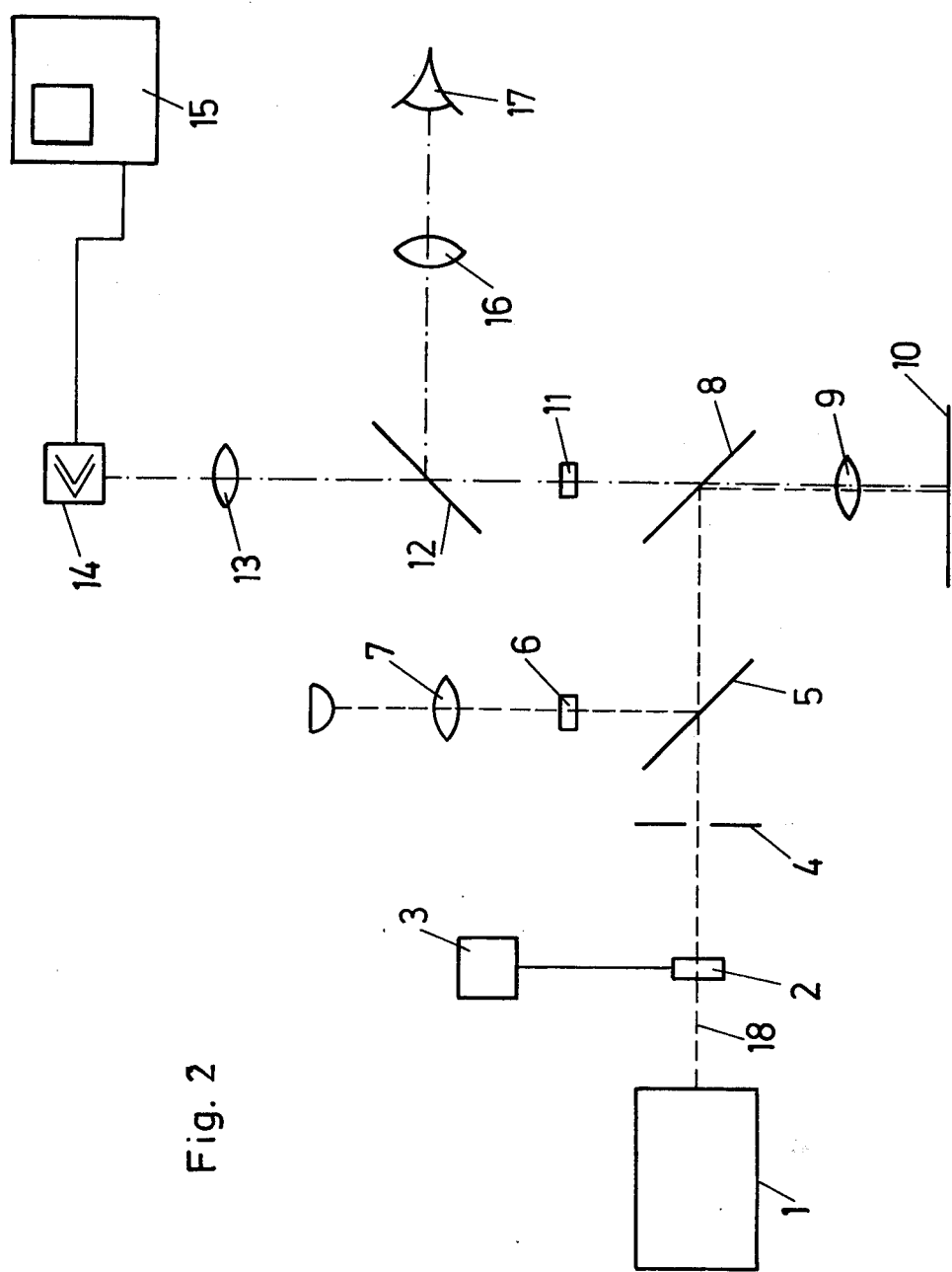
FIG. 2 is a diagrammatic view of a special microscope to be used in accordance with our invention.

The curves shown in FIGS. 1a and 1b were obtained by using an argon-ion laser (Spectra Physics, Mountain View, CA) with a Reichert Zetopan fluorescence microscope serving as the incident-light illumination source. Short pulses (0.1 msec/1 sec) of continuous laser light were generated by means of an acousto-optical shutter device (Soro Optics, Arcueil, France). The pulse duration was governed by an electronically gated high-frequency source. The fluorescence intensities were measured by a fast photodiode, the signal of which was recorded by a storage oscilloscope.

The immunological system consisted of dextran beads (Sephadex G25, superfine) coated with either bovine serum albumin (BSA) or rabbit γ-globulin (RIG) by means of the cyanogen-bromide method. These coated beads served as antigenic substrates in direct immonofluorescence (IF) tests with various concentrations of fluorescein-isothiocyanate-(FITC)-labeled rabbit anti-BSA γ-globulin, and swine anti-RIG γ-globulin (Dakopatts, Copenhagen, Denmark). After incubation with the conjugates (30 min, room temperature), the beads were extensively washed in phosphate-buffered saline (PBS) and thereafter resuspended in a mixture of glycerol:PBS in a 1:1 ratio. Small drops of these suspensions were placed on glass slides and directly covered with cover slips.

For the measurements, beads of various sizes were centered under phase contrast in the area illuminated by a laser beam ($250\mu^2$) and exposed to laser pulses of various duration.

In both systems, the fluorescence measurements revealed that nonspecific adherence of conjugates (anti-BSA/RIG beads and anti-RIG/BSA beads) diluted 1:4 gave fluorescence intensities comparable to those obtained with specifically bound conjugates (anti-BSA/BSA beads, anti-RIG/RIG beads) at dilutions of 1:128. Accordingly, these two concentrations were selected to compare the bleaching characteristics of the nonspecifically versus the specifically bound conjugates. FIG. 1a depicts the bleaching curve for FITC-anti-BSA diluted 1:4 and nonspecifically bound to RIG-coated beads for an excitation period of 10 msec. The shape of this curve is consistent with that of free and protein-bound FITC in aqueous solution, as observed in previous investigations. A marked difference in the fading characteristics was, however, found for the same conjugate (dilution 1:128) bound to beads coated with the homologous antigen, i.e. BSA, as shown in FIG. 1b. It is evident that the steep initial fluorescence decrease observed for the nonspecifically adherent conjugate appears to be markedly lessened when the conjugate is specifically bound to its homolgous antigen. Analogous results were obtained with the anti-RIG conjugate.

The shape of the FITC bleaching curves obtained in the present experiments turned out to be optimally described by the hyperbolic function:

$$FI \sim t^{-1},$$

where FI is the actual fluorescence intensity at a given time $t$. For the mathematical evaluation of individual curves the formula $$FI = \frac{a}{b+t} + c$$

was chosen. Factor $a$ describes the correlation between FI and $t$, $b$ expresses the time-dependent hyperbolic function, and $c$ gives the background fluorescence, which never exceeded 2% of the initial intensity. Values for $b$ were found to differ for specifically and non-specifically bound conjugates in a relation of about 10 to 1.

The following table reproduces the contents of

| t in milli-seconds | FI in Volts | F calculated | t in milli-seconds | FI in Volts | F calculated |
|---|---|---|---|---|---|
| 0.03 | 0.295* | 0.295 | 0.03 | 0.325* | 0.325 |
| 0.04 | 0.275 | 0.27 | 0.04 | 0.32 | 0.32 |
| 0.05 | 0.26 | 0.258 | 0.06 | 0.315 | 0.32 |
| 0.08 | 0.245 | 0.242 | 0.1 | 0.31* | 0.31 |
| 0.09 | 0.24* | 0.24 | 0.2 | 0.3 | 0.3 |
| 0.13 | 0.235 | 0.234 | 0.36 | 0.29 | 0.29 |
| 0.27 | 0.23 | 0.288 | 0.48 | 0.285 | 0.28 |
| 0.65 | 0.225 | 0.225 | 0.71 | 0.275 | 0.27 |
|  |  |  | 0.88 | 0.27* | 0.27 |

$a = 1.35 \cdot 10^{-3}$ V.ms  $\quad a = 19 \cdot 10^{-3}$ V.ms
$b = 0.011$ ms  $\quad b = 0.24$ ms
$c = 0.22$ V  $\quad c = 0.25$ V

*These points were used to determine a, b and c. Afterwards the values in the right column are calculated from the foregoing formula.

The difference in the values obtained for $a$ and $b$ in the two cases is striking. It is obvious that this difference may be used to separate the two types of material.

An experimental set-up which may be used in connection with the method according to the invention is shown in FIG. 2. In this Figure, 1 designates an argon laser (Model 162, 10 mW, Spectra-Physics), 2 is a fast optical shutter (acousto-optic modulator IM 20, SORO ELECTRO OPTICS), 3 is a high-frequency generator, driving the optical shutter, and 4 is a diaphragm.

At a semireflector 5 the laser beam is combined with light from a conventional light source 7 which is followed by a collector and an excitation filter 6. From the semireflector 5 the combined beam reaches a dichroic mirror 8 and is focused on the preparation 10 by the objective 9. The dichroic mirror 8 allows the passage of light emitted by a fluroescent preparation 10. That light reaches a barrier filter 11 and a mirror 12 and is eventually viewed by an observer 17 through an ocular 16 or by means of a photodetector 14 and an oscilloscope 15 after it has passed through another ocular 13.

Figure 2A:
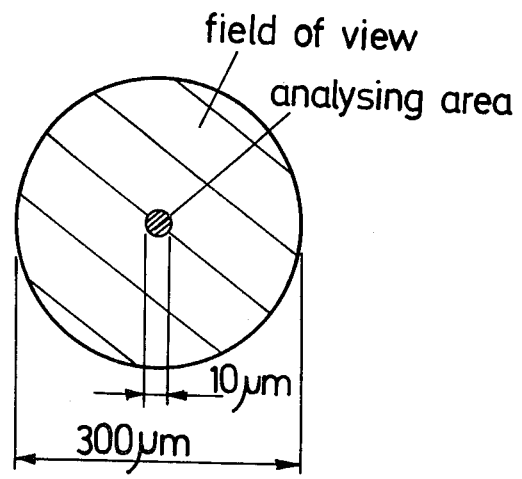
FIG. 2a is an illustration of the field of view of the microscope.

The observer 17 sees a well-lit field of view FIG. 2a, containing fluorescing elements which may be a tissue structure, an organic cell or a carrier matrix with attached material. Any fluorescing element may be brought into the analyzing area illuminated by the laser beam 18, in order to be analyzed for its bleaching characteristics.

Figure 3:
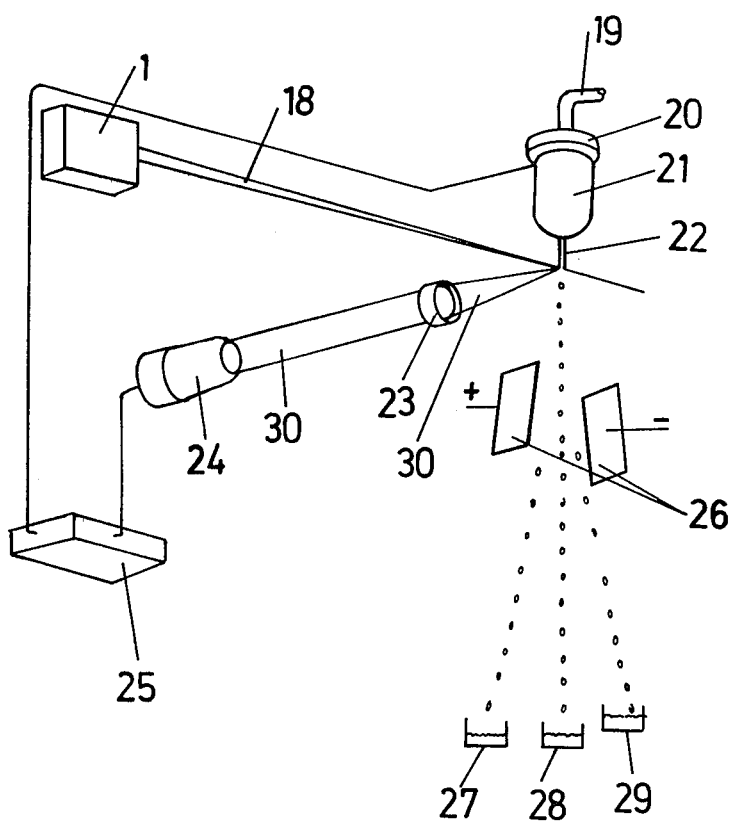
FIG. 3 shows schematically how the invention may be used for the sorting of particles according to their bleaching behavior.

The device shown in FIG. 2 allows for careful scrutiny of individual particles. If, however, it is desired to sort large quantities of particles according to their bleaching characteristics, we prefer to use a device as shown in principle in FIG. 3 which corresponds to a product marketed by Becton & Dickinson as Fluorescence Activated Cell Sorter (FACS). The FACS systems operate as follows: cells in liquid suspension (sample liquid) are injected through tube 19 under pressure into the center of a stream of compatible cell-free fluid (sheath liquid) establishing a laminar, coaxial flow which constrains the cells near the axis of the effluent jet 22 which emerges from a nozzle orifice usually 50 or 60 microns in diameter. The nozzle assembly is vibrated axially, at the rate of 40 kHz, by means of a piezoelectric transducer 20, causing the jet to break into 40,000 uniform droplets per second. Immediately below the nozzle assembly, before droplet formation, the jet is illuminated by the focused light 18 of an argon-ion laser 1, operating at a wavelength selected to excite fluorescence in cells tagged with the appropriate fluorescent stain. Some of the fluorescent light 30 emitted by a stained cell is filtered (at 23) to remove the exciting laser wavelength and is focused onto a photomultiplier tube 24, which generates an electrical signal proportional to the amount of fluorescence of each cell. The signals are processed by the system to produce other electric pulses, which serve to charge the liquid stream exactly when the droplet containing a desired cell is forming. Droplets charged either positively or negatively are directed between two charged plate electrodes 26 and are collected in either on of two vessels 27 and 29 while uncharged droplets flow into the waste vessel 28. In order to be used according to the method of our invention this known device has to be modified insofar as the signal analyzer and sort control unit 25 should no longer respond only to information about the overall intensity of the fluoresence, but should obtain and analyze bleaching curves according to FIGS. 1a and 1b, for each cell before the next cell arrives.

What is claimed is:

1. A method for distinguishing particles or regions therein to which fluorochrome-labeled antibodies or antigens, termed conjugates, are bound by the specific immune reaction of an antibody with its homologous antigen from particles or regions to which the conjugates are nonspecifically bound, comprising illuminating of the particles or regions with a laser, measuring the resulting fluorescence at three or more moments within the first three milliseconds after the beginning of illumination while illumination continues, comparing the observed bleaching behavior of the particle or region with the characteristic curves of specific and nonspecific binding previously obtained by observation of other particles, and producing a signal indicating the type of binding observed.

2. A method according to claim 1 wherein the particles move at an angle through the laser beam, the signal obtained triggering a sorting mechanism separating specifically bound particles from nonspecifically bound ones.

* * * * *